United States Patent
Valkenborg et al.

(10) Patent No.: US 10,598,642 B2
(45) Date of Patent: Mar. 24, 2020

(54) METHOD FOR RELATIVE QUANTIFICATION OF CHEMICAL COMPOUNDS CONTAINED IN A MIXTURE OF DIFFERENT BIOLOGICAL SAMPLES

(71) Applicant: VITO NV, Mol (BE)

(72) Inventors: Dirk Valkenborg, Mol (BE); Jef Hooyberghs, Mol (BE)

(73) Assignee: VITO NV, Mol (BE)

( * ) Notice: Subject to any disclaimer, the term of this patent is extended or adjusted under 35 U.S.C. 154(b) by 441 days.

(21) Appl. No.: 15/362,697

(22) Filed: Nov. 28, 2016

(65) Prior Publication Data

US 2017/0074842 A1 Mar. 16, 2017

Related U.S. Application Data

(63) Continuation-in-part of application No. PCT/EP2015/061823, filed on May 28, 2015.

(60) Provisional application No. 62/003,610, filed on May 28, 2014.

(51) Int. Cl.
| | |
|---|---|
| *G01N 33/487* | (2006.01) |
| *C40B 30/02* | (2006.01) |
| *G01N 30/88* | (2006.01) |
| *G16C 20/70* | (2019.01) |
| *G01N 30/72* | (2006.01) |
| *G16C 20/20* | (2019.01) |

(52) U.S. Cl.
CPC ......... *G01N 30/88* (2013.01); *G01N 30/7233* (2013.01); *G01N 33/487* (2013.01); *G16C 20/70* (2019.02); *G01N 2030/8831* (2013.01); *G01N 2570/00* (2013.01); *G16C 20/20* (2019.02)

(58) Field of Classification Search
CPC ....................................................... G01N 30/88
See application file for complete search history.

(56) References Cited

U.S. PATENT DOCUMENTS

| | | | |
|---|---|---|---|
| 6,334,099 B1 | 12/2001 | Grace et al. | |
| 2012/0208282 A1* | 8/2012 | Deigner .................. | G16B 40/00 436/89 |

FOREIGN PATENT DOCUMENTS

| | | | |
|---|---|---|---|
| EP | 2 270 699 A1 | 1/2011 | |

OTHER PUBLICATIONS

Lahr et al., Bioproportional Techniques in Input-Output Analysis: Table Updating and Structural Analysis, Economic Systems Research, 2004, 16(2), 115-134 (Year: 2004).*
Dittwald et al., BRAIN 2.0: Time and Memory Complexity Improvements in the Algorithm for Calculating the Isotope Distribution, Journal of the American Society of Mass Spectrometry, 2014, 25, 588-594. (Year: 2014).*
Ejigu et al., Evaluation of Normalization Methods to Pave the Way Towards Large-Scale LC-MS-Based Metabolomics Profiling Experiments, OMICS—A Journal of Integrative Biology, 2013, 17(9), 473-485. (Year: 2013).*
Ayrton, A., A Guide to Effective Method Development in Bioanalysis, Waters, 2008, 1-50. (Year: 2008).*
Marshall et al., Creation of a Federated Database of Blood Proteins: A Powerful New Tool for Finding and Characterizing Biomarkers in Serum, Clinical Proteomics, 2014, 11(3), 1-21. (Year: 2014).*
Wisniewski et al., Fast and Sensitive Total Protein and Peptide Assays for Proteomic Analysis, Analytical Chemistry, 2015, 87, 4110-4116. (Year: 2015).*
A. L. Oberg, et al., "Statistical methods for quantitative mass spectrometry proteomic experiments with labeling," Oberg and Mahoney BMC Bioinformatics 2012, 13(Suppl 16):S7—18 pages.
M. Zainol, et al., "Introducing a true internal standard for the Comet assay to minimize intra-and inter-experiment variability in measures of DNA damage and repair," Nucleic Acids Research, vol. 37, No. 22, Oct. 14, 2009, XP55205845, pp. e150-e150, 9 pages.
R. Taubert et al., "Highly variable expression of tissue-restricted self-antigens in human thymus: Implications for self-tolerance and autoimmunity," European Journal of Immunology, vol. 37, No. 3, Feb. 26, 2007, pp. 838-848.
D.E. Bassett, Jr., et al., "Gene Expression Informatics—It's all in your mine," Nature Genetics Supplement, vol. 21, Jan. 1, 1999, pp. 51-55.
International Search Report mailed by European Patent Office dated Aug. 19, 2015 in the corresponding PCT Application No. PCT/EP2015/061823—4 pages.

* cited by examiner

*Primary Examiner* — Amy M Bunker
(74) *Attorney, Agent, or Firm* — Knobbe, Martens, Olson & Bear LLP (57) ABSTRACT

A method is for the simultaneous identification of one or more chemical compounds contained in a sample, from an analytical measurement of a pool of two or more of the samples. A measured intensity of a first and second signal is representative of an abundance of respectively the first and second chemical compound in the first sample, and a measured intensity of a third and fourth second signal is representative of an abundance of respectively a third and fourth chemical compound in the second sample. The first and third, and the second and fourth compound may be the same or different. The signal intensities are organized in a matrix $a_{ij}$ of m columns and n rows, in which n is $\geq 2$ and corresponds to the number of chemical compounds in the pool, and m$\geq$2 and corresponds to the number of samples in the pool.

15 Claims, 2 Drawing Sheets

Fig. 1A and B.

METHOD FOR RELATIVE QUANTIFICATION OF CHEMICAL COMPOUNDS CONTAINED IN A MIXTURE OF DIFFERENT BIOLOGICAL SAMPLES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a method for the simultaneous identification and quantification of two or more chemical compounds contained in a pool of two or more samples, wherein each sample of the pool of samples comprises at least one of the said two or more chemical compounds, wherein the said two or more samples are subjected to a sample equalization before being pooled, wherein sample equalization is carried out in such a way that the total concentration of the chemical compounds in each of the pooled samples is equal, wherein the pool of samples is subjected to an analytical measurement wherein each chemical compound generates at least one signal representative for the said chemical compound and an intensity of each signal is representative for an abundance of the said chemical compound, wherein the intensity of a first and second signal is representative for the abundance of respectively the first and second chemical compound in the first sample, and the intensity of a third and fourth signal is representative for the abundance of respectively a third and fourth chemical compound in the second sample, wherein respectively the first and third, and the second and fourth compound may be the same or different, according to the preamble of the first claim.

The present invention in particular relates to the field of omics, i.e. the simultaneous characterization and quantification of individual biological molecules present in a pool or a mixture of two or more biological samples, for example the characterization and quantification of proteins present in a pool or a mixture of two or more biological samples, or the characterization and quantification of lipids present in a pool or a mixture of two or more biological samples or any other class of biological molecules. Omics involves a.o. metabolomics, lipidomics, genomics and proteomics. The result of such omics reflect the structure, function and dynamics of a biological molecule and of the biological sample.

For example, for the identification and quantification of the biological molecules present in the pool of samples different analytical techniques exist, amongst which NMR spectroscopy, mass spectrometry, microarrays and next-generation sequencing are the most frequently used. To facilitate compound separation, identification and quantification, mass spectrometry may be coupled to liquid chromatography (LC), gas chromatography (GC) or capillary electrophoresis (CE), for example. Each method is typically able to identify a large number of different biomolecules or biomolecules features.

Description of the Related Art

The data generated in metabolomics, proteomics, lipidomics, genomics a.o. usually may be digitized spectra, or lists of the biomolecule levels involved in the respective omics technique. In the simplest form a matrix is generated, with rows corresponding to subjects—identified biomolecules of a certain class, for example peptides present in sample proteins or triglycerides present in lipids—and columns corresponding with biomolecules levels. Statistical programs are available for analysis of these data, for example principal components analysis and least squares regression. Once the molecular composition is determined, data reduction techniques can be used to elucidate patterns and connections.

The fact that in the above-mentioned analytical techniques, in particular in mass spectrometry and NMR, several samples may be pooled and measured in one single experiment, and the fact that a simultaneous identification and/or quantification of biological compounds of different samples may be carried out, benefits a direct statistical assessment, as all the samples of the pool or in other words all the measurements, are affected by the same amount of instrument variability.

Where a relative quantification of e.g. biological molecules is envisaged, labeling of the molecules prior to the analytical measurement gained popularity, because labeling allows multiplexing of samples, in other words pooling of multiple biological samples, so that biological molecules contained in multiple biological samples can be simultaneously quantified. For this purpose, several labeling methodologies have been developed, which can be subdivided in precursor labeling and isobaric labeling. Examples of precursor labeling include metabolic, enzymatic and chemical labeling strategies (Li et al 2012). Metabolic strategies, such as Stable Isotope Labeling by Amino acids (SILAC), are promising but still limited to cell cultures or small animals. As an alternative, both $O^{16}/O^{18}$ enzymatic exchanges as well as chemical isotope labeling approaches such as isotope coded affinity tags (see Lottspeich et al, ICAT) are developed.

The isobaric labeling strategy, for example, belongs to the chemical labeling subclass and is special since the different, yet intact labels have an equal mass, hence the term "isobaric". Isobaric labels are popular in particular in proteomic research as these tags allow multiplexing of up to ten samples in one LC-MS run, which reduces measurement time and makes direct intra experiment comparison possible. The two commercially available kits are Tandem Mass Tags (TMT)(6-plex or 10-plex) and isobaric Tags for Relative and Absolute Quantification (iTRAQ) (4-plex or 8-plex). Both TMT and iTRAQ isobaric tags contain a reporter group and an amino-reactive group, spaced by a balancer group which generates an isobaric mass shift for all tags (Ross, 2004; Thompson 2003). The reactive group of the tag targets N-termini and free amino groups of lysine, so that nearly all digested peptides are labeled at least once. Relative quantification of the labelled and pooled peptides is achieved by the generation of a unique reporter ion upon fragmentation of the peptide precursor. Due to this demultiplexing, the signal intensities of these reporter ions in tandem mass spectra can be used for the determination of the relative expression difference of peptides in the multiplexed samples (Dayon 2008, Zhang 2010, Pichler 2011, Dephoure and Gygi 2012). This multiplexing not only reduces the LC-MS measurement time considerably, it also substantially reduces the variation in the quantification results (Gygi).

This labeling protocol, however, involves additional handling of the samples, which make this isobaric labeling strategy and labeling in general, prone to systematic effects at the level of the wet-lab. One of the most common handling errors, for example, are pipetting errors that occur when samples are pooled (Oberg and Mahoney, 2012) or errors in the determination of the protein concentration prior digestion. This type of inaccuracies can be remediated by data normalization.

To correct for such systematic errors, a plethora of data normalization methods have been developed that can be borrowed from micro-array, LC-MS or NMR data analysis (Ejigu et al 2013, Oberg and Mahoney 2012, Bolstad 2003). Algorithms like quantile normalization (Keshamouni 2005; Jagtap 2006) are often applied in isobaric labelled proteomic studies. Several software packages suited for isobaric labelled data, including Quant (Boehm 2007); IsobariQ (Artnzen 2010); Isobar (breitweiser 2011) use global normalization methods. Here, the intensity distributions of the measurements within a quantification channel are shifted by a constant amount such that the mean or median of the distribution is equal across the quantification channels. Another software package, i-tracker, was developed to establish an easy integration of quantitative information and peptide identification and to provide iTRAQ 4-plex reporter ion ratios (Shadford et al 2005).

SUMMARY OF THE INVENTION

However, the existing normalization methods proved to be insufficient, as they do not permit to fully correct for the systematic effects induced by sample handling and measurement protocols. The present invention therefore seeks to provide a normalization method, with which systematic effects induced by sample handling and measurement protocols may be removed in a more efficient way than actually achieved by the existing normalization techniques.

This is achieved according to the present invention, with a method which shows the technical features of the characterizing portion of the first claim. Thereto the method of the present invention method provides for a method for the simultaneous identification and quantification of two or more chemical compounds in a pool of two or more samples, wherein each sample of the pool of samples comprises at least one of the said two or more chemical compounds, wherein the said two or more samples are subjected to a sample equalization before being pooled, wherein sample equalization is carried out in such a way that the total concentration of the chemical compounds of the pooled samples is equal, wherein the pool of samples is subjected to an analytical measurement wherein each chemical compound generates at least one signal representative for the said chemical compound and an intensity of each signal is representative for an abundance of the said chemical compound, wherein the intensity of a first and second signal is representative for the abundance of respectively the first and second chemical compound in the first sample, and the intensity of a third and fourth signal is representative for the abundance of respectively a third and fourth chemical compound in the second sample, wherein respectively the first and third, and the second and fourth compound may be the same or different, wherein the signal intensities are organized in a matrix aij of m columns and n rows, wherein n is ≥2 and corresponds to the number of chemical compounds in the pool, wherein m≥2 and corresponds to the number of samples in the pool, wherein aij corresponds to a signal intensity measured for a certain signal representative for compound i present in sample j, wherein i=1 to n, and j=1 to m, $$A = \begin{pmatrix} a_{11} & \cdots & a_{1m} \\ \vdots & \ddots & \vdots \\ a_{n1} & \cdots & a_{nm} \end{pmatrix} \quad (1)$$

wherein the rows of said matrix A are subjected to a first scaling constraint such that the mean of each of the rows is equal to 1/m:

$$\sum_j^m a_{ij} = 1 \quad (2)$$

and to a second normalization constraint according to which the mean of the columns of the matrix is equal to 1/m:

$$\sum_i^n a_{ij} = \frac{n}{m} \quad (3)$$

and solving the constrained optimization for this matrix A: minimize $_x f(x)$ subject to $g(x|A)=0$ and determining the abundance of each of the chemical compounds contained in the sample based on the relative content of the corresponding samples in the pool.

BRIEF DESCRIPTION OF THE DRAWINGS

FIGS. 1A and 1B show the log intensity distributions of the six TMT reporter ions before (A) and after (B) normalization according to this invention.

DETAILED DESCRIPTION OF THE PREFERRED EMBODIMENT

In a preferred embodiment of this invention, the two or more chemical compounds belong to a selected class of chemical compounds, as described below. The chemical compounds may for example belong to the class of peptides which originate from certain proteins, triglycerides which originate from certain lipids, saccharides, nucleotides or any other relevant biological molecule.

The present invention in fact provides a data-driven normalization method, which permits to achieve a more accurate normalization of the quantification data of the compounds contained in a pool of samples. The present invention in particular provides a normalization in a data-dependent manner, which permits a more efficient correction or removal of the systematic errors induced by the measurement protocols proper to the analytical technique used to quantify the compounds contained in the pool, than may be achieved with the current normalization techniques known from the art. As a result, the risk to obscuring biological information present in the data, may be reduced to a minimum.

In fact, the method of this invention normalizes the intensity of each signal within an analytical measurement of a pool of samples, such that the average of all present signals in the measurement equals 1/m, m being the number of different samples in the pool.

These constraints aim at modifying the observed intensities to equal amounts whilst controlling them to be proportions by giving limited degrees of freedom.

In the method of this invention it is also assumed that
- the majority of the chemical compounds does not vary between the samples and may be used as a reference set for the normalization, or in other words different samples will in general contain the same chemical compounds, for example protein samples of different origin will contain the same peptides, or lipids samples of different origin will contain the same triglycerides;
- the distribution of up- and downregulated signals or compounds is approximately symmetric
- when systematic errors are made they will affect all intensities measured in the pooled sample, such that the intensity distribution of all the compounds will be influenced
- there is no preference in the generation of certain signals, i.e. all compounds contained in the pool of samples have the same favorable fragmentation properties.

This permits to rescale all signal intensities observed in an analytic measurement, such that the sum of all signal intensities representative for a particular compound measured for the pool of samples, will be equal to one in the case a signal is observed in all samples. In other words, a chemical compound is now quantified by a percentage distribution with respect to the pool of samples, wherein the percentage distribution reflects its abundance in the pooled sample.

These assumptions have the effect that shifts in signal intensity distributions do not originate from a biological effect, but rather from a systematic bias. The present invention therewith allows to carry out an accurate normalization of a mixture of several samples, in a data-dependent manner. Thereby, the quantified chemical compounds are represented as a proportion, for example ⅙th of a sixplex pool of six samples, or ¹⁄₁₀th of a ten-plex pool of ten samples present in a pooled sample.

The present invention thus provides a 'new' matrix Y that deviates least from the original data in X whilst subjected to a set of equality constraints that are imposed by the experimental conditions explained above:

$$Y = \underset{x}{\text{minimize}} f(x \mid X) \text{ subject to } g(x \mid X) = 0$$

In fact, with the present invention equations (2) and (3) above may be generalized to handle data that may contain missing observations and re-written in refined forms to reflect an elegant mathematical symmetry:

$$\frac{1}{m} \sum_{j}^{m} a_{ij} = \frac{1}{m} \rightarrow (A_{i.}) = \frac{1}{m} \quad (4)$$

$$\frac{1}{n} \sum_{i}^{n} a = \frac{1}{m} \rightarrow (A_{.j}) = \frac{1}{m} \quad (5)$$

to provide the final forms of the above-mentioned constraints.

A convenient advantage of this representation is that a downstream statistical analysis does not have to be performed conditionally on the compounds, since each compound contained in a sample is quantified by the relative contribution of the corresponding sample in the mixture or pool of two or more samples. Therefore, the abundance of the compounds within one sample can be compared amongst each other and assembled into compound intensities within one single sample, without requiring further data processing. Without this representation, a conditional statistical analysis would be required to permit quantification of the sample, i.e. in the prior art quantification of the individual components is performed at the level of the component ratios between a practical sample and a control. The use of an external standard as is done in the prior art imposes important restrictions on the flexibility of the experimental design, which may now circumvented by the present invention.

The individual components are not only normalized for each measurement as is done in the known normalization methods, but are rather normalized over an entire experiment, which may involve several subsequent measurements, of one or several subsequent pools of several samples. The present invention thus makes it possible to compare different samples across different runs and distinguishes the method of the present invention from existing normalization approaches. In other words, the method of this invention presents the advantage of being able to maintain the connection with the experimental conditions, while correcting for systematic errors. As a result, the method of this invention may be used to compare different analytical measurements, carried out after another or on different points of time. Thus, the intra-experimental normalization of the present invention permits an inter-experimental comparison of several analytical runs.

In the above, the first and third, and the second and fourth compound may be the same or different, and the first and third and second and fourth signal may be the same or different. Further in the above, m≥2 and corresponds to the number of chemical compounds in the pool and/or to the number of analytical signals used in the matrix, representative for the respective chemical compounds.

In quantile normalization known from the art each experiment is normalized individually. This known individual normalization results in a clustering of the analytical measurements rather than in a clustering of the experimental conditions.

The present invention on the other hand, is capable of handling a pool of several samples which each may contain several chemical compounds, which may be the same or different, and to compare all the analytical data in an intersection of the analytical runs into one normalization procedure. The present invention is particularly capable of handling a pool of several protein samples which each may contain two or more peptides, wherein the peptides of different samples may be the same or different, and to compare all the analytical data in an intersection of the analytical runs into one normalization procedure. This intersection leads towards a data clustering based on experimental groups. As a result, further statistical analysis can be performed directly on the normalized signal intensities, which facilitates rigorous comparison of the experimental groups.

In conclusion, the normalization procedure of the present invention not only opens the possibility of carrying out a normalization within a single analytical measurement of two or more samples, but also permits carrying out an inter-comparison of multiple analytical runs. The present invention therewith provides a method, which permits to remove systematic effects from quantitative data of analytical measurements.

The present invention also permits to calculate data that are missing in an analytical measurement. In case of missing or zero values the constraints simply generalize to the average of the non-missing or non-zero values. In the case of $k_i$ missing values in row i and $k_j$ missing values in column j the constraint can be translated to:

$$\frac{1}{m-k_i}\sum_j^m a_{ij} = \frac{1}{m} \xrightarrow{yields} \sum_j^m a_{ij} = \frac{m-k_i}{m}$$

and $$\frac{1}{n-k_j}\sum_i^n a_{ij} = \frac{1}{m} \xrightarrow{yields} \sum_i^n a_{ij} = \frac{n-k_j}{m}$$

In a preferred embodiment of this invention the signal intensity corresponds to the signal intensity for one or more fragments of the chemical compound.

In a further preferred embodiment of this invention the analytic measurement is a mass spectrometry measurement, and each chemical compound generates m reporter ions or mass signals in the mass spectrum, in a mass spectrum made of a pooled sample which is composed of n samples or n chemical compounds.

In a further preferred embodiment of this invention the two or more chemical compounds are subjected to labelling in advance of the analytic measurement. Labelling of chemical compounds in a pooled sample containing two or more chemical compounds, in particular the use of mass labels, for the relative quantification of the chemical compounds, for example the relative quantification of two or more proteins, allows for multiplexing of several samples, and multiple biological samples may be processed in one analytic measurement, for example one single mass spectrometry measurement or one single liquid chromatography mass spectrometry measurement in a set up where liquid chromatography is combined with mass spectrometry.

It is to be understood that the chemical compounds contained in the pool of two or more samples will usually belong to the same class of chemical compounds, i.e. will be of the same nature, for example the chemical compounds will be peptides, triglycerides, saccharides or nucleotides etc.

Within the scope of this invention several labeling methodologies may be used, for example metabolic, enzymatic and chemical labeling. Preferably however, the two or more chemical compounds are subjected to isobaric labelling, with labels having an equal mass, which generate one or more reporter ions with a unique mass upon fragmentation of the labelled chemical compound into one or more fragments, wherein n represents the number of reporter ions and m represents the number of chemical compounds.

The information presented by the reporter ion intensities for a particular chemical compound, for example a peptide is of a relative nature. Therefore the reporter ion intensities of a peptide may be rescaled to a percentage contribution that reflects the relative proportion of the peptide quantities in the pooled sample. The first constraint therefore ensures that the normalized reporter ion can be interpreted as a percentage. Secondly, during the multiplexing of the individual samples into a pool, the samples are balanced. This has the effect that the pool is composed of equimolar concentrations of the chemical compounds, for example proteins, from the multiplexed samples. The second constraint thus ensures that the reporter ion intensities reflect equal concentrations and removes the systematic bias from the data due to sample handling errors, for example pipetting errors, Several methods are available to the skilled person to solve a constrained optimization as described above. The symmetry in the constraints allows to use a straightforward methodology that originates from the field of econometrics.

Suitable methods that are well known to the skilled person include the RAS-method (Stone et al, 1942; Bacharach, 1970) or more general, the Iterative Proportional Fitting procedure (IPFP) (Deming and Stephan, 1940; Fienberg, 1970). The method of this invention fits into the requirements for the procedure to converge to a unique solution.

The RAS procedure, also known as raking in computer science, estimates two diagonal matrices $\hat{S}$ and $\hat{N}$ that represent the scale and normalization parameters used to transform the original data matrix. Diagonal matrix $\hat{S}$ is an n by n matrix that contains a scaling parameter for each identified peptide i and diagonal matrix $\hat{N}$ is an m by m matrix that contains a normalization parameter for each quantification channel j. As such, m+n degrees of freedom are at our dispose to optimally transform the original data such that it comply with the proposed constraints. In matrix notation:

$$Y = f(x|X) = \hat{S}X\hat{N} \quad (6)$$

The procedure iterates between a scaling step (2) and a normalization step (3) until convergence is obtained
  % Start normalization
  1. Initialize procedure $$\hat{A}_0 = \overline{A} \Leftrightarrow \hat{A}_0 = \begin{pmatrix} \overline{a}_{11}^0 & \cdots & \overline{a}_{1m}^0 \\ \vdots & \ddots & \vdots \\ \overline{a}_{n1}^0 & \cdots & \overline{a}_{nm}^0 \end{pmatrix}$$

% Start loop at t=0, t=0, 1, 2, . . . , T, where t=T is the last iteration wherein convergence is reached.
  2. Scaling step
    Calculate scaling parameter:

$$\hat{C}_{t+1} = \begin{pmatrix} c_1^{t+1} & \cdots & 0 \\ \vdots & \ddots & \vdots \\ 0 & \cdots & c_n^{t+1} \end{pmatrix} \text{ with } c_i^{t+1} = \frac{1/m}{\text{Mean}_j(a_{ij}^{2t})}$$

Scale data:

$$\hat{A}_{2t+1} = \hat{C}_{t+1} \times \hat{A}_{2t}$$

3. Normalization step
    Calculate normalization parameter:

$$\hat{d}_{t+1} = \begin{pmatrix} d_1^{t+1} & \cdots & 0 \\ \vdots & \ddots & \vdots \\ 0 & \cdots & d_m^{t+1} \end{pmatrix} \text{ with } d_j^{t+1} = \frac{1/m}{\text{Mean}_i(a_{ij}^{2t+1})}$$

Normalize data:

$$\hat{A}_{2t+2} = \hat{A}_{2t+1} \times \hat{d}_{t+1}$$

4. If $(\hat{A}_{2t+2} - \hat{A}_{2t}) > \varepsilon$ –with $\varepsilon$ a small error, then stop the loop, t=T else t=t+1
  % End loop
  5. Assign final result:

$$A = \hat{A}_{2T+2}$$

Although the RAS procedure returns the constrained standardized data, the diagonals of the scale and normalization matrix can be easily calculated as:

$$\hat{S} = \left(\prod_t^T \hat{c}_{t+1}\right) \text{ and } \hat{N} = \left(\prod_t^T \hat{d}_{t+1}\right) \text{ with } t = 0, 1, 2, \ldots, T \quad (7)$$

The step-wise progress of the RAS algorithm by how much current row sums deviate from the prespecified row marginal is measured, and by how much column sums deviate from the column marginals. To this end the L1-error function is introduced:

$$err(t) = \frac{1}{2}\sum_i^n |A_{i.}(t) - 1/m| + \frac{1}{2}\sum_j^m |A_{.j}(t) - 1/m|$$

For odd steps t, rows match their prespecified marginals and the row error sum vanishes. For even steps t the column error sum is zero, as it is then the columns that attain their marginals.

When implementing the algorithm, use is made of the following stopping criteria: $err(t) < \Delta_{abs}$ where $\Delta_{abs}$ is a user defined threshold typically of order 1E-4. From the datasets, the algorithm reaches convergence after 20 iterations. This number of iterations may vary based on the amount of data, the error in the data and the user specified threshold $\Delta_{abs}$.

The method of the present invention is suitable for use with a wide variety of analytical techniques, in which a signal is representative for a chemical compound or a fragment thereof and a signal intensity is representative for the abundance of a chemical compound in a sample, for example infrared spectroscopy, NMR spectroscopy and mass spectroscopy, but also SIMS, ESR and any other known analytical technique. Where the invention is used for the quantification of chemical compounds in a pool of samples using mass spectrometry, preferably, the mass spectrometer is preceded by a technique, which permits separation of the compounds contained in the pooled sample, for example a liquid chromatograph (LC), a gas chromatograph (GC) or capillary electrophoresis (CE).

It is remarked that independently of the nature of the chemical compounds used to form a pool which is subjected to the identification and quantification method of this invention, each of the samples forming the pool are subjected to a sample equalization before being pooled, in such a way that the total concentration of the chemical compounds contained in each sample of the pooled samples is equal.

It is further remarked that in a preferred embodiment of this invention, the two or more chemical compounds belong to a selected class of chemical compounds as described below.

It is within a preferred embodiment of this invention that the one or more biomolecular compounds correspond to one or more fragments of a polymeric compound. Polymeric compounds are to be understood in the most general way, i.e. any molecule comprising two or more building units. Examples include organic as well as inorganic compounds, for example an ester, an ether, a polyester, an ether, a polyether, a fatty acid, a mono-, di- or triglyceride, a polyalkylene, a polyoxyalkylene, a silicate, a siloxane, a polysiloxane, a mineral, an aluminasilicate, a magnesium silicate, a magnesiumaluminate, an organic or inorganic carbonate, a claim mineral, a zeolite or a mixture of two or more of the afore-mentioned compounds. It is to be understood that the present invention is suitable for use with any chemical compound that may be subjected to an analytical measurement with the purpose of quantifying the chemical compound or its fragments.

It is within a particularly preferred embodiment of this invention that the one or more chemical compounds are selected from the group of one or more biomolecules and one or more fragments or metabolites or precursors of the one or more biomolecules.

The present invention is particularly suitable for use with omics, i.e. the simultaneous characterization and quantification of of individual biological molecules present in a pool or a mixture of two or more biological samples. The result of such omics reflect the structure, function and dynamics of a biological sample. The present invention is particularly suitable for use in proteomics, the large scale study of proteins and peptides; lipidomics, i.e. studying the pathways and network of lipids the large scale study of lipids; genomics the large scale study of genes and gene transcripts; and metabolomics, the large scale study of metabolites, i.e. the study of the chemical fingerprints of cellular processes. The metabolome represents the collection of metabolites in a biological cell, tissue, organ or organism, which result from cellular processes and provides information on the physiology thereof, more in particular the chemical structure of the afore mentioned compounds.

In the method of the present invention the biomolecule may be a metabolome, i.e. a small-molecule metabolite, for example a metabolic intermediate, a hormone or another signaling molecule, or a secondary metabolite which originate from a biological sample, in particular an organism.

According to the method of this invention, two or more metabolome of two or more different organisms may be pooled and analysed in a single measurement or experiment, for example amino acids, organic acids, nucleic acids, fatty acids, amines, sugars, vitamins, co-factors, pigments, antibiotics, wherein the exogenous metabolite includes one or more compounds selected from the group of drugs, environmental contaminants, food additives, toxins and other xenobiotics that are not naturally produced by an organism.

Examples of biomolecules suitable for use with the present invention include genes or fragments thereof, DNA, mRNA, rRNA, tRNA and other non-coding RNA or fragments thereof; proteins, polypeptides, peptides, amino acids; lipids, phospholipids, triglycerides, fats, fatty acids; carbohydrates, metabolites and fragments of the afore mentioned biomolecules, and mixtures of two or more of the afore-mentioned biomolecules.

The biomolecule may originate from widely varying sources, and may for example originate from a tissue or a biofluid. The biomolecule may either be endogeneous or exogeneous.

Within the scope of the present invention, the chemical compounds may be subjected to analysis as such, or the chemical compound may be subjected to labeling in advance of subjecting them to the envisaged analytical measurement. Labeling techniques are well known to the skilled person, the skilled person is able to select an appropriate labeling technique taking into account the nature of the chemical compound, in particular the biologic molecule to be analysed. When labeling is applied, the analytical measurement will rather concentrate on measuring the associated labels.

The method of the present invention is particularly suitable for the analysis of proteins, whereby the protein may be subjected to either precursor labeling or isobaric labeling in advance of LC-MS analysis. The present invention implies a constrained satisfaction problem to estimate a set of scale and normalization parameters. Isobaric labels used in proteomic research allow multiplexing of up to ten samples in one LC-MS run, which reduces measurement time and makes direct intra experiment comparison possible. This is especially advantageous when more than eight or ten biological samples (iTRAQ/TMT) are measured in a quantitative experiment, for example a quantitative proteomics experiment to detect different peptides with sufficient statistical power.

It is known in the art to add a pool as a reference sample in a labeled design, which can be used as a normalization factor (ref. 16, 17). As explained above, this normalization procedure ignores parameters such as handling errors, which are specimen specific (ref. 4). More advanced techniques working with peptide level abundance values in stead of abundance ratios, including quantile normalization and Cyclic Loess normalization, provide good normalization methods for one TMT multiplex, for example one TPT sixplex experiment (ref. 18). However, when two or more multiplex experiments need to be compared, these methods have their shortcomings. The present invention is capable of bypassing this limitation by the intra-experimental normalization of the present invention that facilitates an inter-experimental comparison of different and several measurement runs, for example LC-MS runs.

In quantile normalization known from the art, each TMT experiment is normalized individually, which results in clustering of the TMT experiments rather than in clustering of the experimental conditions. The present invention on the other hand allows one to combine all the samples that have to be measured, and thus to compare all components in an intersection of the different measurements, into one normalization procedure, leading towards a clustering based on experimental groups. Thus, further statistical analysis can be performed directly on the normalized component intensities, for example peptide intensities, from a particlular compound, for example a particular protein, meaning that the statistical analysis is not performed on the peptide ratios, which facilitates rigorous comparison of these experimental groups.

Thus, the present invention provides a new method for determining the composition of a biologic sample, which currently does not exist for the analysis of 2D- and 1D-LC-MS/MS experiments where isobaric labels are used to obtain quantitative information. The present invention herewith provides a method within which a multiplex measurement method may be carried out, but moreover also permits carrying out an inter-comparison of multiple isobaric measurements, in particular LC-MS/MS runs.

The invention is further illustrated in the example below.

Example

Sample Preparation

Three different types of immune cells, each originating from six biologically independent samples were used.

For the three different types of immune cells, which correspond to three different experimental conditions, the cell pellets were lysed using 200 µl RIPA buffer (1×) (Thermo Scientific, Waltham, Mass.) with 1× HALT protease inhibitor and 1× HALT phosphatase inhibitor (Thermo Scientific), combined with 3×10 s sonication (Branson Sonifier SLPe ultrasonic homogenizer, Labequip, Ontario, Canada) of the sample on ice. After centrifugation of the samples for 15 min at 14,000 g and 4° C., the cell pellet was discarded. Then, the protein concentration was determined using the Pierce BCA protein Assay kit (Thermo Scientific).

Next, 15 µg of each protein sample was reduced using 2 µl of 50 mM tris(2-carboxyethyl) phosphine, supplied with the TMT labeling kit (available from Thermo Scientific), in a volume of 100 µl 100 mM triethylammoniumcarbonate (TEAB), and incubated for 1 h at 55° C. After alkylation of the sample with 375 mM iodoacetamide and 30 min incubation in the dark, six volumes of ice-cold acetone were added to each sample. Afterwards, the samples were incubated at −20° C. overnight. The next day, the samples were centrifuged at 6000 g and 4° C. for 10 min followed by the removal of the acetone. Next, the protein pellet was resuspended in 15 µl of 100 mM TEAB solution. To improve further solubilization of the proteins and to assure efficient digestion, 0.1% Rapigest SF surfactant (Waters, Milford, Mass.) was added to the sample, followed by an incubation of 5 min at 100° C. To digest the proteins, trypsin Gold (Promega) was added in an enzyme:protein ratio of 1:20, and the sample was incubated overnight at 37° C. The next day, Rapigest was inactivated and trypsin digestion was stopped by the addition of 200 mM HCl to the samples, followed by a 30 min incubation at ambient temperature. After a centrifugation step of 5 min at 14,000 g, the supernatant was collected and stored at −80° C. until further use.

TMT Labeling

For the reconstitution of the tags, the TMT labels were dissolved in 41 µl acetonitrile according to the manufacturer's protocol. From every sample, 10 µg of protein was labeled with 4.1 µl of a TMT tag dissolved in acetonitrile, and every sample was incubated for 1 hour at ambient temperature. The labeling reaction was stopped by adding 1 µl 5 mM hydroxylamine. After 15 minutes, a pooled sample was prepared based on the labeled samples with a protein concentration ratio of 1:1:1:1:1:1. Next, the labeled digests were desalted using Pierce C18 spin columns (Thermo Scientific) according to the manufacturer's instructions. An overview of the experimental set-up can be found in Table 1. It should be noted that the 18 samples that belong to three experimental conditions (three different cell types termed A, B and C) are block-randomized over the available TMT labels such that two biological replicates of each condition are present in a pooled sample for analysis on LC-MS.

TABLE 1

An overview of the experimental set-up. Three different experimental conditions (A, B and C) from 6 subjects. Each sixplex has 2 biological replicates of each experimental group.

|  | TMT 126 | TMT 127 | TMT 128 | TMT 129 | TMT 130 | TMT 131 |
|---|---|---|---|---|---|---|
| Run 1 | C1 | A1 | B1 | B2 | A2 | A2 |
| Run 2 | A3 | B3 | C4 | A4 | C3 | B4 |
| Run 3 | C5 | A6 | B5 | A5 | C6 | B6 |

Reversed-Phase Liquid Chromatography and Mass Spectrometry

To reduce the complexity, the labeled samples were fractionated offline with an Acquity ultra-high pressure liquid chromatography (UPLC) system (Waters). The TMT-labeled peptide mixtures were reconstituted with 30 µl of mobile phase A (2% ACN, 1% NH$_4$OH, 0.25% FA, pH=9). The samples were loaded onto an X-bridge BEH130 C18 column with following dimensions: 50 mm×2.1 mm and 5 µm particles (Waters). The peptides were eluted at a flow rate of 1.5 ml/min with a linear gradient of 2% mobile phase B (95% ACN, 4% NH$_4$OH, 0.5% FA, pH=9) to 60% mobile phase B over 10 min. The peptide elution was monitored by measuring the absorbance at λ=214 nm with a photodiode array, and fractions were collected at 1 minute intervals. The resulting fractions were dried in a vacuum concentrator (Eppendorf).

Each fraction was further separated by reversed-phase chromatography on an Eksigent nano-UPLC system using an Acclaim C18 PepMap100 nano-Trap column (200 μm×2 cm) connected to an Acclaim C18 analytical column (75 μm×15 cm, 3 μm particle size) (Thermo Scientific, San Jose, Calif.). Before loading, the sample was dissolved in 15 μl of mobile phase A (0.1% formic acid in 2% acetonitrile) and spiked with 20 fmol Glu-1-fibrinopeptide B (Glu-fib, Protea Biosciences, Morgantown, W. Va.). A linear gradient of mobile phase B (0.1% formic acid in 98% acetonitrile) from 2 to 35% in 110 min followed by a steep increase to 95% mobile phase B in 2 min was used at a flow rate of 350 nl/min. The nano-LC was coupled online with the mass spectrometer using a PicoTip Emitter (New Objective, Woburn, Mass.) coupled to a nanospray ion source (Thermo Scientific).

The LTQ Orbitrap Velos (Thermo Scientific, San Jose, Calif.) was set up in MS/MS mode where a full scan spectrum (350-2000 m/z, resolution 60,000) was followed by a maximum of five dual CID/HCD tandem mass spectra (100-2000 m/z). Peptide ions selected for further interrogation by tandem MS were the five most intense peaks of a full-scan mass spectrum. CID scans were acquired in the linear ion trap of the mass spectrometer, HCD scans in the orbitrap, at a resolution of 7500. The normalized collision energy used was 40% in CID and 55% in HCD. We applied a dynamic exclusion list of 90 s for data-dependent acquisition. The entire wet-lab and LC-MS procedures were controlled for confounding factors.

Data Analysis

Proteome discoverer (1.3) software (Thermo Scientific, San Jose, Calif.) was used to perform database searching against the IPI Human 3.87 database using both Sequest and Mascot algorithms. Following settings were applied: precursor mass tolerance of 10 ppm, fragment mass tolerance of 0.8 Da. Trypsin was specified as digesting enzyme and two missed cleavages were allowed. Cysteine carbamidomethylation and TMT modifications (N-terminus and lysine residues) were defined as fixed modifications and methionine oxidation and phosphorylation on serine, threonine and tyrosine residues were variable modifications. The results were filtered using the following settings: Only medium and high confident peptides with a global FDR<5% and first-ranked peptides were included in the results. In the TMT quantitation workflow the most confident centroid method was used with an integration window of 20 ppm. The reporter ion intensities were corrected for isotope contamination by solving a system of linear equation and using the known label purity values from the data sheet [12]. In this study, all the sequences and reporter ion intensities of the unique peptides that match the previously mentioned requirements were exported to comma-separated-values for further data analysis.

Normalization Principles

In isobaric labeling procedures, a normalization method is required to remove systematic bias such that the biological information present in the data is not obscured. Therefore, we present a data-driven normalization approach that exploits the principles of the isobaric labeling process.

In order to develop an algorithm which can normalize this systematic effect, the following assumptions were made:

1) the majority of proteins do not vary between samples and are used as a reference set for the normalization. As a consequence, expression profiles from extreme experimental conditions, e.g., different pull-downs should be avoided 2) the distribution of up- and downregulated proteins are approximately symmetric 3) when systematic errors are made, they will affect all peptide intensities in the pooled sample, such that the intensity distribution of all the peptides will be influenced.

These assumptions entail that shifts observed in reporter intensity distributions most likely do not originate from a biological effect, but from a systematic bias.

Further, it was assumed that there is no preference in the generation of the reporter fragment ions, i.e. that all the isobaric labels have the same favorable fragmentation properties. Hence, it was assumed that reporter intensities reflect the relative abundance of a peptide in the pooled sample. Because of these assumptions, the reporter ion intensities may be presented on a relative scale. For this purpose, the intensities were rescaled such that their sum for a particular peptide will be equal to one. In other words, peptides are now quantified by a percentage contribution that reflects their abundance in the pooled sample.

In an ideal situation the peptide concentration in the pooled samples should be equal because they are equalized in the pool by the bicinchoninic acid (BCA) protein concentration assay prior to digestion. In other words, the sample is pooled such that the global protein concentration is equal across the reporter channels, i.e., a ratio of 1:1:1:1:1:1. This sample equalization prior to pooling should result in equal reporter intensity distributions, therefore, the mean values of the peptide intensities in a quantification channel are set to 1/m for an isobaric labeling experiment that contains m labels. A commonly applied normalization method, such as global normalization will center the intensity towards a user-defined value that corresponds to shifting the intensity distributions up or down. However, applying such normalization that shifts the distribution to 1/m would invalidate our interpretation of the percentage contribution of the sample in the pool. Therefore, a constraint should be applied during the data normalization.

A constraint was applied such that the sum of the reporter intensities is equal to one, and normalized such that the mean of the observed intensity distribution was equal to 1/m. It was aimed to modify the observed intensities to equal amounts whilst controlling them to be proportions by giving only limited degrees of freedom: one coefficient per peptide and one coefficient per reporter channel.

The data that originate from an m-plex isobaric labeling experiment can be represented in a rectangular data format. This format is an m by n data matrix $\bar{A}$ as presented in equation (1) that collects the information about the reporter ion intensities from a tandem mass spectrum. The columns of this matrix denote the m quantification channels that correspond to the multiplexed samples, whilst the rows represent the n peptides that are identified in the LC-MS experiment. More formally, each element $\bar{a}_{ij}$ in matrix $\bar{A}$ represent the absolute intensity of a peptide i in reporter channel j.

$$\hat{A} = \begin{pmatrix} \bar{a}_{11} & \cdots & \bar{a}_{1m} \\ \vdots & \ddots & \vdots \\ \bar{a}_{n1} & \cdots & \bar{a}_{nm} \end{pmatrix} \quad (1)$$

With the indices, i=1, 2, ..., n and j=1, 2, ..., m. Formally, we consider a normalization process A=$\mathcal{H}$ ($\bar{A}$) that produces a new normalized matrix A given the original data matrix $\bar{A}$. Imposed by the experimental conditions explained in the previous paragraph, the resulting matrix A should satisfy the following constraints in case of a complete data matrix (no missing values)

$$\sum_{j}^{m} a_{ij} = 1 \quad (2)$$

and $$\sum_{i}^{n} a_{ij} = \frac{n}{m} \quad (3)$$

where $a_{ij}$ is an element of the normalized data matrix A. These two constraints are equivalent to $\text{mean}_j(a_{ij})=1/m$ and $\text{mean}_i(a_{ij})=1/m$. In case of missing values this simply generalizes to the mean over the non-missing values.

Equations (2) and (3) are denoted as scaling constraint and normalization constraint, respectively. Recall that the restriction in equation (2) ensures that the normalized intensities can be interpreted as a percentage contribution of sample j in the pool for a particular peptide i. The restriction in equation (3) scales the distribution of the normalized intensities towards a mean value of 1/m such that the reporter intensities of each multiplexed sample reflect an equal contribution in the protein/peptide concentration in the pool.

To represent the strengths of the algorithm of the present invention, the above-described normalization method was applied to a standard TMT sixplex quantitative experiment, where 3×6 samples (representing 18 biologically independent samples from 3 experimental groups) are randomized and measured in three TMT sixplex LC-MS experiments. An overview of the experimental set-up is given in Table 1. FIG. 1 represents the comparison of data prior to and after normalization. Here, log-intensity distributions of the six reporter channels (numbered from 1 to 6, representing the reporter channels TMT 126 to TMT 131) are visualized using boxplots.

Figure 1A:
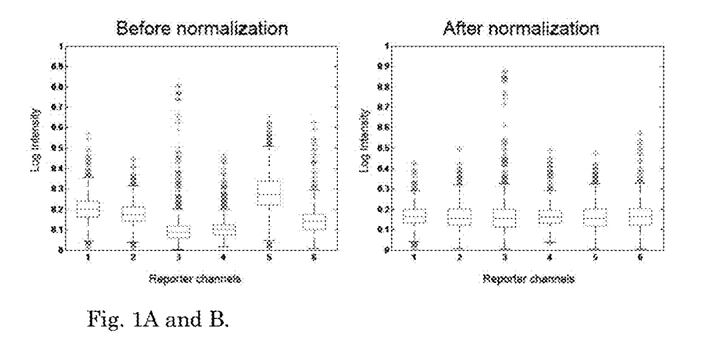

FIG. 1 represents the comparison of data prior to and after normalization. From FIG. 1A, it becomes clear that small systematic error, e.g. pipetting errors, influence the intensity distribution of all the peptides in the sample. Because the sample is pooled in a ratio of 1:1:1:1:1:1, its intensity distribution should be equal across the reporter channels. Each systematic wet-lab error that is present in a sixplex experiment can be detected as shifts (up or down) in the transformed distribution of intensities in a reporter channel.

For this purpose, the normalization of the present invention rescales the intensities such that the sum of their reporter intensities equals to one. In the case of TMT sixplex, the peptide content in the pooled sample is normalized such that the mean of the reporter intensities are equal to ⅙ of the total sample. This rescaling is illustrated in FIG. 1b. From FIG. 1b, it can be observed that the intensity distribution is centered on the ⅙%. This percentage representation has already been suggested by Shadforth et al [12], however, the normalization was not restricted by the constraint in equation (3). A convenient artefact of this representation is that a downstream statistical analysis has no longer to be performed conditionally on the peptides as each peptide is quantified by the relative contribution of a sample in the pooled sample. Therefore, they can be compared or assembled into protein intensities without further processing. Without this representation a conditional statistical analysis is required to quantify the protein content, i.e., the protein quantification is performed at the level of peptide ratios between a case and a control. This latter scheme imposes important restrictions on the flexibility of the experimental design, which are now circumvented by the representation of the present invention.

The constraint standardization according to the present invention of the data is executed by a algorithmic procedure from the field of economics, called the RAS algorithm [13] or more generally known as the iterative proportional fitting procedure [14, 15].

Next, the method of the present invention is compared to the popular quantile normalization technique which is often employed to standardize microarray data. The validity of the normalization is assessed by a clustering analysis that assembles the measured peptide intensities for the three TMT sixplex experiments in the study. It should be noted that clustering is done on the subset of peptides that were identified and quantified in the 3 sixplex LC-MS/MS experiments (intersection). In case of quantile-normalized intensities (FIG. 2A), the clustering fails to group subjects that are connected to the same experimental groups. Instead, the clustering algorithm groups the subjects that were pooled in the same multiplexed LC-MS experiments. The grouping of subject according to the same LC-MS experiment illustrates that clustering is driven by the systematic errors still present in the data and that biological information is obscured by these errors. However, when looking within the LC-MS experiment of the pooled sample, it can be noticed that the clustering does group subjects that are related to each other. Hence, for comparing samples within an isobaric labeling experiment the quantile normalization seems sufficient.

Figure 2:
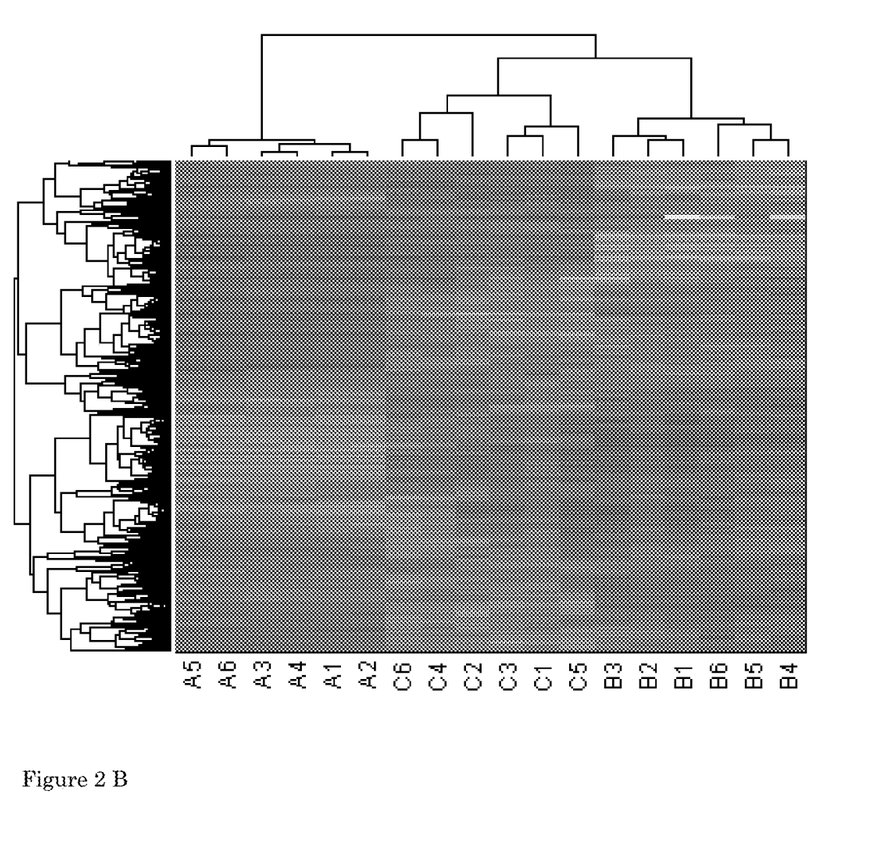
FIGS. 2A and 2B show hierarchical clustering with quantile normalization (A) and normalization according to this invention (B).
Figure 2A:
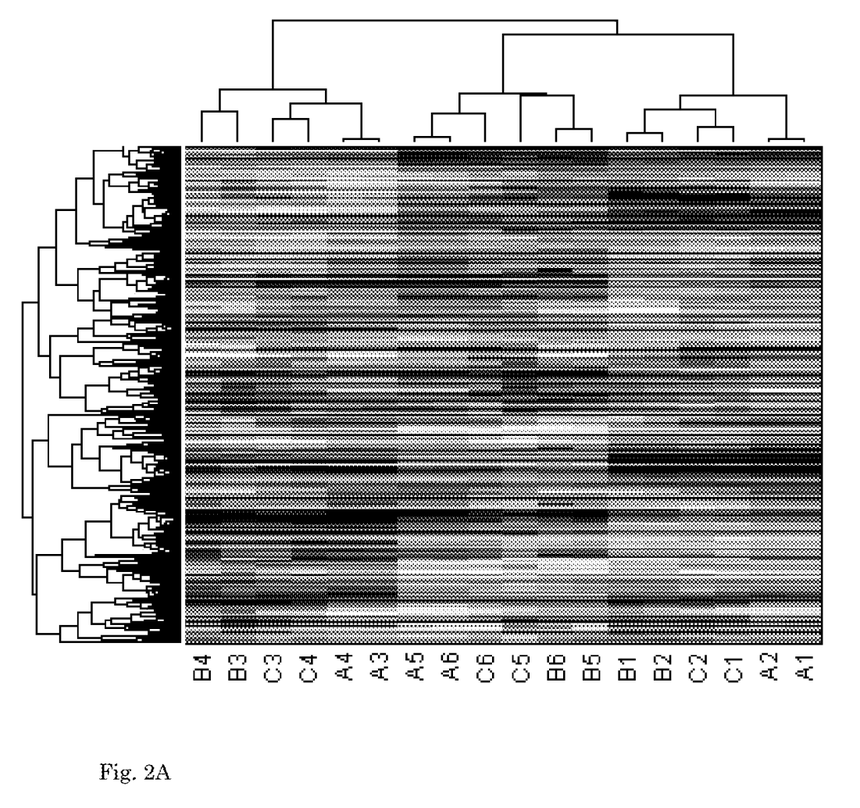

On the other hand, clustering of the intensities normalized according to the present invention assembles the data such that they correspond to the biological subclasses (FIG. 2B). This correct grouping illustrates that systematic nuisances from the LC-MS measurements are removed, whilst biological relevant information is maintained and, as a result, further statistical analysis can be performed on the peptide intensities.

REFERENCES

1. Dayon, L., Hainard, A., Licker, V., Turck, N. et al. Relative quantification of proteins in human cerebrospinal fluids by MS/MS using 6-plex isobaric tags. Anal. Chem. 2008, 80 (8), 2921-2931.
2. McAlister, G. C., Huttlin, E. L., Haas, W., Ting, L. et al. Increasing the multiplexing capacity of TMTs using reporter ion isotopologues with isobaric masses. Anal. Chem. 2012, 84 (17), 7469-7478.
3. Ross, P. L., Huang, Y. N., Marchese, J. N., Williamson, B. et al. Multiplexed protein quantitation in *Saccharomyces cerevisiae* using amine-reactive isobaric tagging reagents. Mol. Cell Proteomics 2004, 3 (12), 1154-1169.
4. Oberg, A. L., Mahoney, D. W., Statistical methods for quantitative mass spectrometry proteomic experiments with labeling. BMC. Bioinformatics. 2012, 13 Suppl 16, S7.
5. Ejigu, B. A., Valkenborg, D., Baggerman, G., Vanaerschot, M. et al. Evaluation of normalization methods to pave the way towards large-scale LC-MS-based metabolomics profiling experiments. OMICS. 2013, 17 (9), 473-485.
6. Bolstad, B. M., Irizarry, R. A., Astrand, M., Speed, T. P., A comparison of normalization methods for high density oligonucleotide array data based on variance and bias. Bioinformatics. 2003, 19 (2), 185-193.

7. Keshamouni, V. G., Michailidis, G., Grasso, C. S., Anthwal, S. et al. Differential protein expression profiling by iTRAQ-2DLC-MS/MS of lung cancer cells undergoing epithelial-mesenchymal transition reveals a migratory/invasive phenotype. J. Proteome Res. 2006, 5 (5), 1143-1154.
8. Jagtap, P., Michailidis, G., Zielke, R., Walker, A. K. et al. Early events of *Bacillus anthracis* germination identified by time-course quantitative proteomics. Proteomics 2006, 6 (19), 5199-5211.
9. Boehm, A. M., Putz, S., Altenhofer, D., Sickmann, A., Falk, M., Precise protein quantification based on peptide quantification using iTRAQ. BMC. Bioinformatics. 2007, 8, 214.
10. Arntzen, M. O., Koehler, C. J., Barsnes, H., Berven, F. S. et al. IsobariQ: software for isobaric quantitative proteomics using IPTL, iTRAQ, and TMT. J. Proteome Res. 2011, 10 (2), 913-920.
11. Breitwieser, F. P., Muller, A., Dayon, L., Kocher, T. et al. General statistical modeling of data from protein relative expression isobaric tags. J. Proteome Res. 2011, 10 (6), 2758-2766.
12. Shadforth, I. P., Dunkley, T. P., Lilley, K. S., Bessant, C., i-Tracker: for quantitative proteomics using iTRAQ. BMC. Genomics 2005, 6, 145.
13. Lahr, M., de Mesnard, L., Biproportional Techniques in Input-Output Analysis: Table Updating and Structural Analysis. Economic Systems Research 2004, 16 (2), 115-134.
14. Deming, W. E., Stephan, F. F., On a Least Squares Adjustment of a Sampled Frequency Table When the Expected Marginal Totals are Known. Ann. Math. Statist. 1940, 427-444.
15. Fienberg, S. E., An Iterative Procedure for Estimation in Contingency Tables. Ann. Math. Statist. 1970, 907-917.
16. Bortner, J. D., Jr., Richie, J. P., Jr., Das, A., Liao, J. et al. Proteomic profiling of human plasma by iTRAQ reveals down-regulation of ITI-HC3 and VDBP by cigarette smoking. J. Proteome Res. 2011, 10 (3), 1151-1159.
17. Amelina, H., Sjodin, M. O., Bergquist, J., Cristobal, S., Quantitative subproteomic analysis of age-related changes in mouse liver peroxisomes by iTRAQ LC-MS/MS. J. Chromatogr. B Analyt. Technol. Biomed. Life Sci. 2011, 879 (30), 3393-3400.
18. Kall, L., Vitek, O., Computational mass spectrometry-based proteomics. PLoS. Comput. Biol. 2011, 7 (12), e1002277.
19. Ting, L., Rad, R., Gygi, S. P., Haas, W., MS3 eliminates ratio distortion in isobaric multiplexed quantitative proteomics. Nat. Methods 2011, 8 (11), 937-940.

What is claimed is:

1. A method for the simultaneous identification and quantification of two or more protein compounds contained in a pool of two or more samples, the method comprising;
   (a) subjecting the two or more samples to a sample equalization before being pooled, wherein the sample equalization is carried out in such a way that the total concentration of the two or more protein compounds in each of the two or more samples is equal, wherein the sample equalization comprises:
      (i) determining a total amount of each of the two or more protein compounds;
      (ii) subjecting the same amount of the two or more protein compounds to an enzymatic digestion; and
      (iii) labeling fragments of the two or more protein compounds for a mass spectrometry measurement, such that concentrations of the two or more protein compounds are equal in said two or more samples, and equal concentrations of the two or more protein compounds are subjected to the mass spectrometry measurement for the simultaneous identification and quantification of the two or more protein compounds to obtain a signal intensity representative of the two or more protein compounds, wherein the signal intensity corresponds to the signal intensity for one or more fragments of the two or more protein compounds;
   (b) pooling the two or more samples; and
   (c) subjecting the pool of the two or more samples to an analytical measurement using the mass spectrometry measurement, wherein each of the two or more protein compounds generates at least one signal that is representative for each of the said two or more protein compounds and an intensity of each signal is representative for an abundance of each of the two or more protein compounds, wherein the intensity of a first and second signal is representative for an abundance of respectively a first and second protein compound in a first sample, and the intensity of a third and fourth signal is representative for an abundance of respectively a third and fourth protein compound in a second sample, wherein respectively the first and third, and the second and fourth compound are the same or different, wherein the signal intensities are normalized in a matrix aij of m columns and n rows, wherein n is an integer >2 and corresponds to the number of said two or more protein compound in the pool, wherein m>2 and corresponds to the number of samples in the pool, wherein aij corresponds to a signal intensity measured for compound i present in sample j, wherein i=1 to n, and j=1 to m, $$A = \begin{pmatrix} a_{11} & \cdots & a_{1m} \\ \vdots & \ddots & \vdots \\ a_{n1} & \cdots & a_{nm} \end{pmatrix} \quad (1)$$

wherein the rows of said matrix A are subjected to a first scaling constraint such that the mean of each of the rows is equal to 1/m:

$$\sum_{j}^{m} a_{ij} = 1 \quad (2)$$

and to a second normalization constraint according to which the mean of the columns of the matrix is equal to 1/m:

$$\sum_{i}^{n} a_{ij} = \frac{n}{m} \quad (3)$$

and solving a constrained optimization for this matrix A: minimize xf(x) subject to g(x|A)=0 and
   (d) determining the abundance of each of the two or more protein compounds contained in the two or more samples based on the relative content of the corresponding two or more samples in the poof wherein the normalization is conducted by rescaling the signal intensities with the formulas (1)-(3) to remove systematic errors, such that a risk of obscuring biological information present in the two or more samples is reduced to a minimum, wherein the following assumptions are under the normalization:
   (i) a majority of the two or more protein compounds do not vary between the two or more samples;
   (ii) a distribution of up- and down-regulated signal intensities of the two or more protein compounds is approximately symmetric between the two or more samples; and
   (iii) systematic errors affect all the signal intensities of the two or more protein compounds in the two or more samples.

2. The method according to claim 1, wherein a missing value or a zero value in matrix A is calculated by generalizing the missing or zero value to the mean of the non-missing or non-zero values as follows:

$$\frac{1}{m-k_i}\sum_{j}^{m} a_{ij} = \frac{1}{m} \xrightarrow{yields} \sum_{j}^{m} a_{ij} = \frac{m-k_i}{m}$$

and $$\frac{1}{n-k_j}\sum_{i}^{n} a_{ij} = \frac{1}{m} \xrightarrow{yields} \sum_{i}^{n} a_{ij} = \frac{n-k_j}{m}.$$

3. The method according to claim 1, wherein the analytical measurement is a mass spectrometry measurement and each protein compound of the two protein compounds generates m reporter ions in the mass spectrometry measurement, in a mass spectrum of n two or more protein compounds.

4. The method according to claim 1, wherein the two or more protein compounds are subjected to labelling in advance of the analytical measurement.

5. The method according to claim 4, wherein the two or more protein compounds are subjected to isobaric labelling, with labels having an equal mass, which generate one or more reporter ions with a unique mass upon fragmentation of the labelled two or more protein compounds into one or more fragments, wherein n represents the number of reporter ions and m represents the number of the two or more protein compounds.

6. The method according to claim 1, wherein the two or more protein compounds are selected from the group consisting of two or more biomolecules, two or more biomolecule fragments, metabolites of the two or more biomolecules, and precursors of the two or more biomolecules.

7. The method according to claim 6, wherein the two or more biomolecules are selected from the group consisting of genes, proteins, peptides, lipids, carbohydrates, and precursors, metabolites, and fragments of the afore-mentioned two or more biomolecules, and mixtures of the afore-mentioned two or more biomolecules.

8. The method according to claim 6, wherein the metabolites of the two or more biomolecules is selected from the group consisting of a metabolic intermediate, a hormone, and a secondary metabolite which originates from a biological sample.

9. The method according to claim 6, wherein the metabolites of the two or more biomolecules are selected from the group consisting of endogenous metabolites, exogenous metabolites, and a mixture of two or more endogenous metabolites and/or exogenous metabolites of the two or more biomolecules.

10. The method according to claim 9, wherein the endogenous metabolites of the two or more biomolecules include one or more compounds selected from the group consisting of amino acids, organic acids, nucleic acids, fatty acids, amines, sugars, vitamins, co-factors, pigments, and antibiotics.

11. The method according to claim 9, wherein the exogenous metabolites of the two or more biomolecules includes one or more compounds selected from the group consisting of drugs, environmental contaminants, food additives, and toxins.

12. The method according to claim 6, wherein the two or more biomolecules are selected from the group consisting of DNA, mRNA, rRNA, tRNA, and other non-coding RNA.

13. The method according to claim 1, wherein the two or more samples are selected from the group consisting of an organ, a tissue, a biofluid, and a part of an organ, tissue, or biofluid.

14. The method according to claim 13, wherein the biofluid is selected from urine and plasma.

15. The method according to claim 6, wherein the two or more biomolecules are a protein and one or more peptides of the protein that have been subjected to precursor labeling or to isobaric labeling.

* * * * *

UNITED STATES PATENT AND TRADEMARK OFFICE
CERTIFICATE OF CORRECTION

PATENT NO. : 10,598,642 B2
APPLICATION NO. : 15/362697
DATED : March 24, 2020
INVENTOR(S) : Dirk Valkenborg et al.

Page 1 of 2

It is certified that error appears in the above-identified patent and that said Letters Patent is hereby corrected as shown below:

In the Specification

In Column 1, Line 27, delete "measurement" and insert -- measurement, --.

In Column 3, Line 61, delete "aij" and insert -- $a_{ij}$ --.

In Column 3, Line 64, delete "aij" and insert -- $a_{ij}$ --.

In Column 5, Line 45, delete "$Y = \underset{x}{\text{minimize}} f(x|X) \text{ subject to } g(x|X) = 0$" and insert -- $Y = \underset{x}{\text{minimize}} f(x|X) \text{ subject to } g(x|X) = 0$ --.

In Column 7, Line 67, delete "errors," and insert -- errors. --.

In Column 9, Line 66, delete "aluminasilicate," and insert -- aluminosilicate, --.

In Column 10, Line 14, delete "of of" and insert -- of --.

In Column 10, Line 28, delete "afore mentioned" and insert -- afore-mentioned --.

In Column 10, Line 48, delete "afore mentioned" and insert -- afore-mentioned --.

In Column 10, Line 53, delete "endogeneous" and insert -- endogenous --.

In Column 11, Line 17, delete "in stead" and insert -- instead --.

In Column 11, Line 38, delete "particlular" and insert -- particular --.

Signed and Sealed this
Twenty-eighth Day of July, 2020

Andrei Iancu
*Director of the United States Patent and Trademark Office*

CERTIFICATE OF CORRECTION (continued)
U.S. Pat. No. 10,598,642 B2

In the Claims

In Column 18, Line 28, Claim 1, delete "aij" and insert -- $a_{ij}$ --.

In Column 18, Line 29, Claim 1, delete "integer>2" and insert -- integer$\geq$2 --.

In Column 18, Line 30, Claim 1, delete "m>2" and insert -- m$\geq$2 --.

In Column 18, Line 32, Claim 1, delete "aij" and insert -- $a_{ij}$ --.